Figure 1:
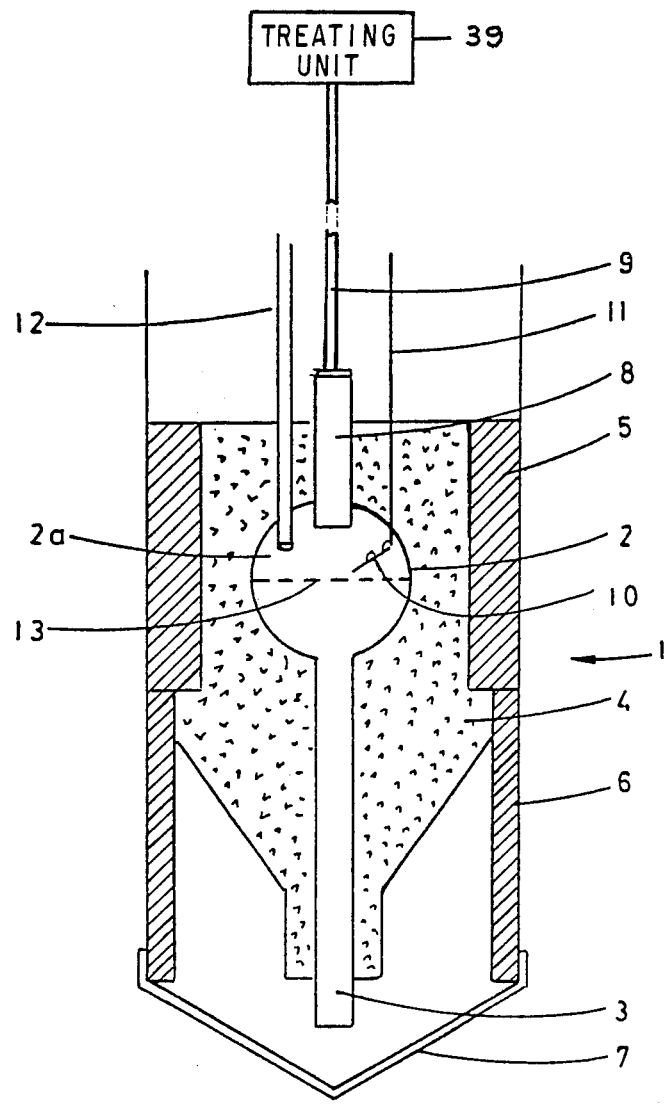

United States Patent [19]

Kumbrant

[11] Patent Number: 4,732,477
[45] Date of Patent: Mar. 22, 1988

[54] ANALYZING PROBE

[75] Inventor: Lars Kumbrant, Orsundsbro, Sweden

[73] Assignee: Geotronics Metaltech AB, Orsundsbro, Sweden

[21] Appl. No.: 2,941

[22] Filed: Jan. 13, 1987

Related U.S. Application Data

[63] Continuation of Ser. No. 665,172, Oct. 26, 1984, abandoned.

[30] Foreign Application Priority Data

Oct. 27, 1983 [SE] Sweden ................................. 8305914

[51] Int. Cl.$^4$ ............................................. G01N 21/67
[52] U.S. Cl. ................................. 356/313; 73/DIG. 9
[58] Field of Search .............. 356/36, 313; 73/DIG. 9

[56] References Cited

U.S. PATENT DOCUMENTS

| | | | |
|---|---|---|---|
| 3,645,628 | 2/1978 | Bojic et al. ......................... | 356/313 |
| 3,659,944 | 5/1972 | Bojic ................................... | 356/313 |
| 4,037,478 | 7/1977 | Cure .................................. | 73/DIG. 9 |
| 4,102,197 | 7/1978 | Bardenheuer et al. ........... | 73/DIG. 9 |

FOREIGN PATENT DOCUMENTS 1066039 9/1959 Fed. Rep. of Germany ...... 356/313

Primary Examiner—F. L. Evans
Attorney, Agent, or Firm—Witherspoon & Hargest

[57] ABSTRACT

The present invention briefly refers to a device and a method for analyzing samples of molten charges inside the charges themselves. An analyzing probe (1) comprising a body (4) of ceramic material with an inlet for molten charge is provided in a tube (5) of board or the like and forms a disposable probe. A cavity (2a) is provided in the ceramic body (4) and the inlet (3) has a notch or the like towards the cavity for receiving molten charge. An electrode (10) is positioned in the cavity (2a) and upon application of electric current via the electrode (10) and the molten charge a spark or a luminous arc is ignited between the electrode (10) and the portion of the sample of the molten charge adjacent the notch. A light-conducting body (8) is provided in the cavity adjacent the luminous arc or sparks for collecting light emitting therefrom.

7 Claims, 4 Drawing Figures

ANALYZING PROBE

This is a continuation of application Ser. No. 665,172, filed on Oct. 26, 1984, now abandoned.

The present invention refers to analyzation of molten charges and in particular to a device for direct analysis of molten charges in respect to their composition.

At present all analysis of molten charges is performed on the basis of samples drawn from the molten charge with the aid of a sampler. These samplers have to be submerged into the molten charge or must be filled in some other way with the molten material and the sample drawn must thereafter be removed from its mould, cooled to a temperature permitting management, be transported tor the laboratory, prepared for treatment and subsequently be exposed to various types of analyses.

Such a handling is time-consuming and the sample may be exposed to undesirable changes during cooling and transport. Moreover such samples are subjected to quick oxidation after having been exposed to the oxygen of the air.

Many advantages might be gained if the analyzation of the molten charge could be performed as close to the charge as possible and most preferably directly in the molten charge, for example by submerging into the charge a probe from which signals are transmitted to a treating unit, for example an optical emission spectrometer for direct display of the composition of the molten charge. Hereby it would be possible without delay to obtain a sample analysis which means that the time required for obtaining the analysis result would be shortened from an order of magnitude of minutes to seconds. Such a reduction of the time required would mean that the proper time when the molten charge is ready could be established with great exactitude whereby a morebetter product would be obtained.

It would be a further advantage of such a direct analysis of molten charges that the work and equipment necessary at present for handling, preparing samples and analyzing them could be saved.

It is a purpose of the present invention to remove the above-mentioned drawbacks of presently applied methods for drawing and analyzing samples. This purpose is realized by an analyzing probe for direct excitation by means of a luminous arc or a spark within the molten charge, said analyzing probe being defined in the claims which also indicate the characteristic features of the invention. An object of the invention is also a method of performing a direct analysis of the composition of a molten charge.

Figure 2:
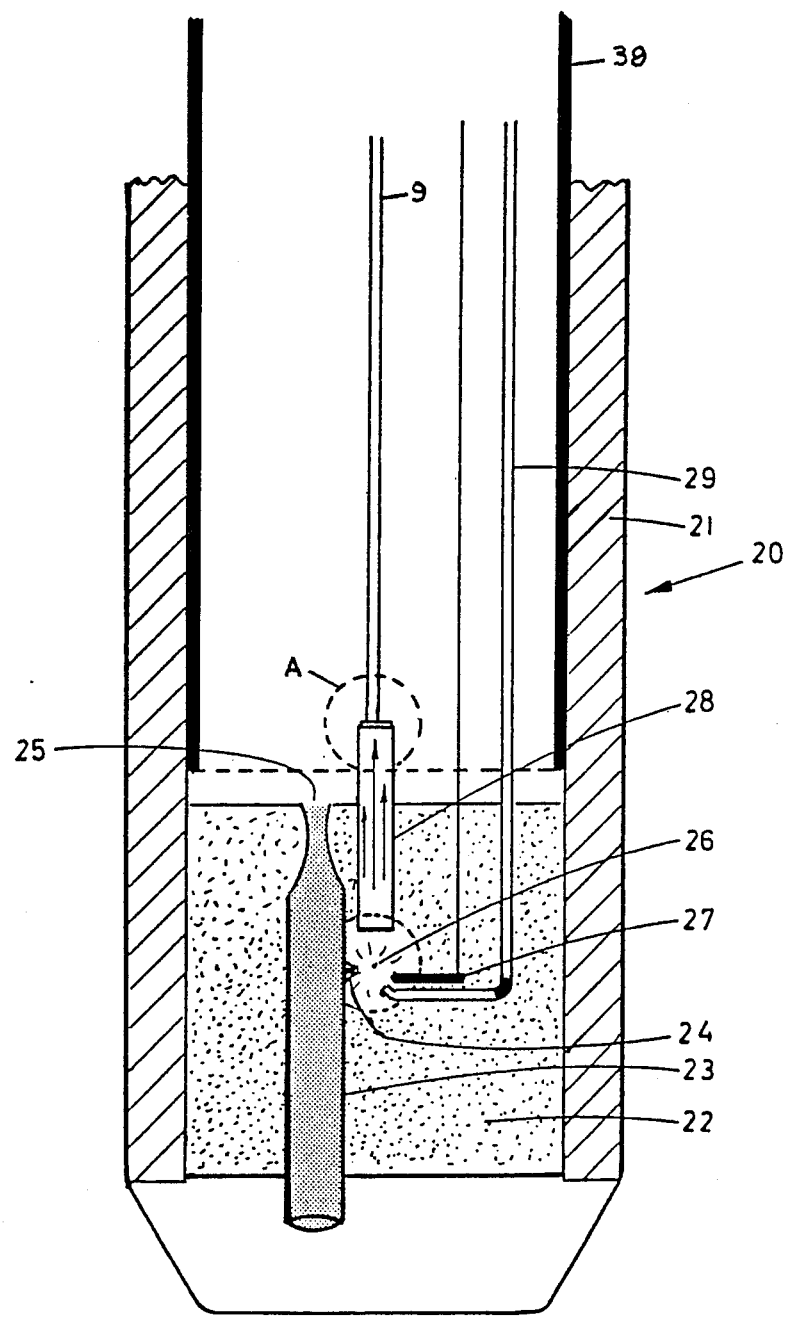
Figure 3:
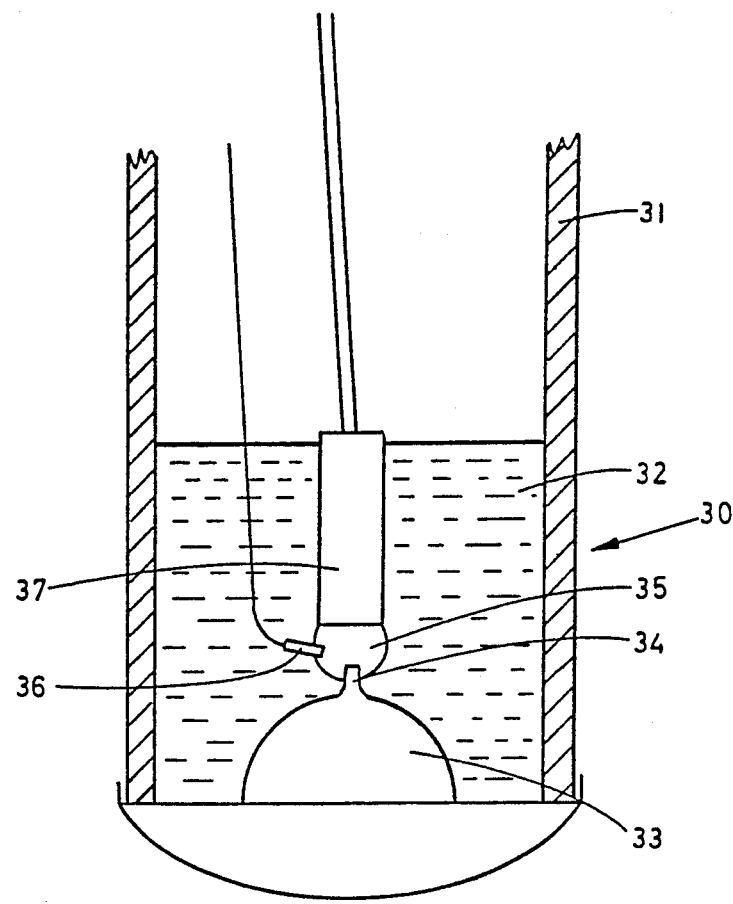
Figure 4:
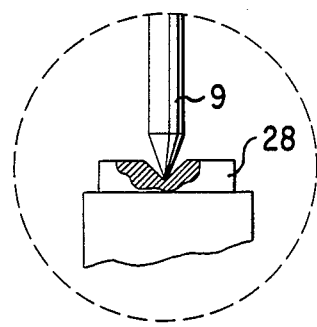

The invention will be more closely described by reference to the attached drawings in which FIG. 1 is a schematic section of an embodiment of the analyzing probe according to the invention, FIG. 2 is a similar section of a second embodiment of the analyzing probe according to the invention, FIG. 3 is a similar section of a third embodiment of an analyzing probe according to the invention, and FIG. 4 is a partial section view of area A of FIG. 2.

The analyzing probe shown in FIG. 1 comprises a mould 2 having a cavity 2a and an inlet tube 3 embedded in a body 4 of ceramic material. The ceramic body 4 is attached to the end of a surrounding tube 5 of board or other suitable material. The ceramic body 4 has circular cross-section and the inlet tube 3 which suitably consists of quartz glass, extends slightly from the end of the body facing away from the board tube 5. A protective sleeve 6 surrounds this part of the ceramic body 4 extending from the end of the board tube 5 and a slag protection 7 covers the end of the analyzing probe.

The analyzing probe 1 described so far is substantially a conventional sampler the use of which is well known to the experts on this field. However, the novel feature of this construction is constituted by a light-transmitting body 8 such as a quartz rod, positioned with its one end in the cavity 2a of the mould 2 and extending at the other end a distance from the end of the ceramic body 4 enclosed within tube 5. This light-conducting body 8 has a connection, not shown, to a fibre-optical light conductor 9 extending upwardly through a sample rod, not shown, to a treating unit such as some suitable form of a spectrometer 39.

Moreover, an electrode 10 is positioned within the mould 2 and connected via a conduit 11 through the rod to a suitable current source. To prevent oxidation of the sample of the molten charge flowing into the mould 2 an inlet tube 12 for inert gas such as argon communicates with the cavity 2a in the mould 2.

The analyzing probe 1 according to the invention as shown in FIG. 1 operates in the following way:

With the aid of the mentioned rod, not shown, the analyzing probe 1 is submerged into the molten charge in the ordinary way. After some time the slag protection 7 will melt away and molten charge will flow through the inlet tube 3 and into the mould 2. If deoxidizing of the sample in the mould 2 is desired, suitble means for this purpose are provided in connection to the inlet tube 3.

At the same time as molten charge is flowing into the cavity through tube 3 inert gas is blown into the mould 2 through tube 12 creating a counter-pressure in cavity 2a so that the molten charge will be halted and solidified to form a counter electrode substantially on the level marked by the broken line 13, that means slightly below the electrode 10. A voltage is appied to electrode 10 which consists of wolfram or any other suitable material not interfering with the analysis, and aluminous arc or a spark is formed between the electrode and the sample of the charge in the cavity 2a of mould 2. The light from the arc or sparks is collected by the light-conducting body 8 and is transmitted through the fibre-optical conductor 9 to the treating unit not shown.

The gas supplied through tube 12 has not only the function to constitute a counter-pressure and to prevent oxidation of the sample but has the additional function to maintain an atmosphere in cavity 2a between the sample and the light-conducting body 8 which does not disturb the spectrum which the luminous arc or the sparks emit but enables all the wave lengths to be transmitted to the treating unit.

Such an analyzation may be performed within some few seconds and supplies with the aid of the treating unit an immediate information regarding the composition of the molten charge.

The embodiment of the invention illustrated in FIG. 2 has the same basic function of the embodiment according to FIG. 1. However, there are certain constructive differences. The analyzing probe 20 shown in FIG. 2, thus, comprises a tube 21 of board or the like adapted to be attached in a conventional way at e.g. a sampling rod 38 and in the end of which a body 22 of ceramic material is inserted. An inlet tube 23 for molten charge is inserted into the ceramic body with one end opening into the wall positioned within the end of the board-tube 21. Inlet tube 23 is suitably axially positioned and has a radial opening 24 with small area, the inner end of the inlet tube 23 terminating in a corresponding opening 25 of small area.

The radial opening 24 opens into a cavity 26 and substantially opposite to this opening 24 an electrode 27 is provided. Between the opening 24 and the electrode 27 a spark gap is formed and adjacent thereto a light-conducting body 28 is provided catching the light from the luminous arc. Suitably a tube 29 for supplying an inert gas is also in communication with the cavity 26.

The analyzing probe 20 according to FIG. 2 acts in the same way as the one shown in FIG. 1. Due to the specific construction of the inlet tube 23 no counter-pressure gas needs to be supplied because the molten charge after having reached opening 24 will solidify immediately after passage therethrough and will form a counter-electrode to electrode 27. The same thing will happen when the molten charge has reached the opening 25 where it also will solidify. As soon as the molten charge will have reached opening 24 and started solidifying the luminous arc or the sparks may be ignited and the light will be collected by the light-conducting body 28 which will happen prior to any oxidation.

In FIG. 3 a third embodiment of the analyzing probe according to the invention is shown. In the same way as the previously described probes this analyzing probe 30 comprises a tube 31 of board or the like including a body 32 of ceramic material. In contrast to the other samplers the present embodiment is not provided with an inlet tube. In stead there is provided a depression 33 in the outwardly facing wall of the ceramic body 32, this depression 33 having an opening 34 of small area communicating with a cavity 35 corresponding to the cavities previously described.

In connection to the cavity 35 an electrode 36 and a light-conducting rod 37 are provided. Preferably there will be also as tube, not shown, for supplying an inert gas to the cavity 35 as well as ducts, not shown, for venting the depression 33.

Fundamentally the third embodiment of the analyzing probe according to the invention operates in the same way as the previously described two embodiments.

Irrespective of the embodiment chosen, an analyzing probe according to the present invention is intended to be used only once in order to guarantee correct conditions. Obviously the invention might be realized in the form of a probe adapted to be used several times and such a probe is also intended to fall within the scope of the invention. However, in certain connections it can be desirable to save the sample, for example for the sake of documentation, and in such a case it is suitable to break out the sample left in the inlet tubes or the like causing the analyzing probe itself to be destroyed.

In connection with the embodiments shown and described it has been stated that the molten charge in the inlet tube or the like initially is exposed adjacent the electrode. However, this is not necessary per se and the inlet tube or the like may be provided with a notch or the like where the discharge form the electrode may strike through the inlet tube to establish contact with the sample of the molten charge.

Such a notch may be in the form of an attenuation, a cnductive coating on the outside of the tube, an extra electrode or the like. From the above teaching it will appreciated that the expert may apply many such variations which, however, must be considered to be within the scope of the invention as defined in the attached claims.

I claim:
1. A disposable sampler for drawing a sample from a molten charge, said sampler being adapted to be mounted on a means such as a rod, for submerging the sampler into the molten charge, said means comprising a fibre-optical light conductor for transferring light signals from the sampler to an analyzing device, said sampler comprising:
   a body of ceramic material having a cavity;
   means forming a part of said body, and including an inlet, for facilitating flow of said molten material into said cavity, halting said molten material in said cavity, and solidifying said molten material to form a counter electrode in said cavity;
   an electrode extending into said cavity, adapted to ignite a spark or luminous arc between said electrode and said counter electrode in said cavity;
   means for applying a voltage to said electrode; and
   a light conducting body in the form of a rod and provided with a connection with said fibre-optical light conductor, said light conducting body extending into said cavity adjacent the position where said spark or arc is to be ignited.

2. The sampler of claim 1 wherein said inlet comprises a tube having an opening with a small area opening into said cavity.

3. The sampler of claim 1 wherein said inlet comprises a depression formed in said body of ceramic, a wall which forms said depression having an opening of small area whic opens into said cavity.

4. The sampler of claim 1 wherein a gas supply tube extends into said cavity.

5. The sampler of claim 1 further including means in communication with said cavity for supplying inert gas into said cavity.

6. A disposable sampler for drawing a sample from a molten charge, said sampler being adapted to be mounted on a means such as a rod, for submerging the sampler into the molten charge, said means comprising a fibre-optical light conductor for transferring light signals from the sampler to an analyzing device, said sampler comprising:
   a body of ceramic material having a cavity, one end of said body of ceramic material being enclosed within an end of a surrounding tube and another end of said body of ceramic material extending away from said tube;
   means forming part of said body, and including an inlet, for facilitating flow of said molten material into said cavity, holding said molten material in said cavity, and solidifying said molten material to form a counter electrode in said cavity, said inlet extending from said end of said body of ceramic material extending away from said tube;
   an electrode extending into said cavity, adapted to ignite a spark or luminous arc between said electrode and said counter electrode in said cavity;
   means for applying a voltage to said electrode; and,
   a light conducting body in the form of a quartz rod positioned with one end extending into said cavity and the other end extending a distance from said one end of said body of ceramic material enclosed within an end of said surrounding tube, said other end of said rod being adapted for connecting to one end of said fibre-optical light conductor extending upwardly through said submerging means.

7. The sampler of claim 6 further including means in communication with said cavity for supplying inert gas into said cavity.

* * * * *